United States Patent
Wang et al.

(10) Patent No.: US 7,354,570 B2
(45) Date of Patent: Apr. 8, 2008

(54) CHINESE PREPARATION FOR TREATING ENTERITIS ULCER COLITIS AND PREPARATION METHOD THEREOF

(75) Inventors: Bihui Wang, Beijing (CN); Zhixin Guo, Tianjin (CN); Zhengliang Ye, Tianjin (CN); Shunnan Zhang, Tianjin (CN)

(73) Assignee: Tianjin Kinsly Pharmaceutical R&D Co., Ltd., Beichen District, Taijin (CH)

( * ) Notice: Subject to any disclaimer, the term of this patent is extended or adjusted under 35 U.S.C. 154(b) by 15 days.

(21) Appl. No.: 10/507,149

(22) PCT Filed: Mar. 5, 2003

(86) PCT No.: PCT/CN03/00166

§ 371 (c)(1),
(2), (4) Date: Aug. 16, 2005

(87) PCT Pub. No.: WO03/075937

PCT Pub. Date: Sep. 18, 2003

(65) Prior Publication Data

US 2006/0003026 A1    Jan. 5, 2006

(30) Foreign Application Priority Data

Mar. 8, 2002    (CN) ............................... 02 1 04050

(51) Int. Cl.
*A61K 8/97* (2006.01)
*A61K 8/27* (2006.01)
*A61K 33/06* (2006.01)
*A61K 36/889* (2006.01)

(52) U.S. Cl. .......................... 424/58; 424/67; 424/684; 424/727

(58) Field of Classification Search ............ None
See application file for complete search history.

(56) References Cited

U.S. PATENT DOCUMENTS

| 4,017,615 | A | * | 4/1977 | Shastri et al. | ............... | 514/174 |
| 5,538,728 | A | * | 7/1996 | Yanaki et al. | ............... | 424/401 |
| 5,800,817 | A | * | 9/1998 | Verge et al. | ................ | 424/770 |
| 6,383,524 | B2 | * | 5/2002 | Tao | ............................ | 424/725 |

FOREIGN PATENT DOCUMENTS

| CN | 1202361 A | * | 12/1998 |
| CN | 1051236 C | * | 4/2000 |

* cited by examiner

*Primary Examiner*—Susan Coe Hoffman
*Assistant Examiner*—Catheryne Chen
(74) *Attorney, Agent, or Firm*—Fish & Richardson P.C.

(57) ABSTRACT

This invention provides a preparation of traditional Chinese medicinal materials for the treatment of ulcerative colitis and the processed method thereof. The preparation of present invention is prepared from Sanguis Draxonis, etc. The processed method of the preparation comprises the steps of (a) decocting Radix Paeoniae Rubra, Catechu and Calcined Alumen with water; (b) mixing Indigo Naturalis and Sanguis Draxonis thoroughly, with PEG solution added; (c) mixing the sifted Rhizoma Bletillae, the above-mentioned aqueous decoction and the Indigo Naturalis and Sanguis Draxonis in PEG solution thoroughly, followed by adding Halloysitum Rubrum and Calamina thereto and grinding together, finally the enema is prepared after water being added. The enema of present invention is highly effective in the short- and long-term pharmacological treatment of ulcerative colitis.

15 Claims, No Drawings

CHINESE PREPARATION FOR TREATING ENTERITIS ULCER COLITIS AND PREPARATION METHOD THEREOF

FIELD OF THE INVENTION

The present invention is related to the preparation of traditional Chinese medicinal materials for the treatment of ulcerative colitis and the processed method thereof.

BACKGROUND OF THE INVENTION

Ulcerative colitis or Non-specific colitis (CUC) is referred to as a type of chronic colitis without known causes. Said disease causes lesion (mostly ulcer) that usually occurs on the mucosa of colon and also extends throughout the colon. The fatality rate of CUC in acute stage is high, and cancer is feasible to be induced in the chronic stage. The clinical cardinal symptom of CUC comprises abdominal pain, diarrhea, bloody purulent stool and tenesmus. The pathological course of CUC is protracted and the attacks repeat frequently. Recently, there is an upward tendency of onset with said disease, attacking people at any age, affecting more male than female. So far, the pathogenesis of said disease is still unknown and it suggests that the onset of CUC relates to immunity, heredity, infection and mental stress. Most scholars incline to the view, however, that CUC is involved in not only the autoimmune mechanism, but also the heredity tendency.

In Traditional Chinese Medicine, ulcerative colitis (UC) is deemed as falling into the categories of "chronic diarrhea", "dysentery", "Intestine attacked by wind" and "poison in Zang-organ" and the like. The pathogenesis of said disease is mostly concerned with being caught in Summer-heat and Cold-dampness, or the internal injury caused by eating the cold, or the internal injury in the Spleen and Stomach, yun-hua abnormality, or downward flow of Damp-pathogen to large intestine, yun-jie bu-jie, rendering the stagnation of Fu-Qi in the Stomach and Intestine, or the stagnation of Qi and Blood followed by combined Dampness or Cold-dampness.

Currently, the clinical therapy for the UC comprises various methods, which is classified as Western medical therapy, Traditional Chinese therapy and Acupunctural therapy.

Western Medical Therapy

At present, the Western medical therapy uses medicines comprising norfloxacin, salicylazo sulfapyridine (SASP), immune depressant, corticosteroid and Metronidazole etc. However, due to the complexity of UC, such as relapsing course of UC and the treatment slow in effect, serious adverse effect is easily arisen in the long-term administration of Western medicine.

Acupuncture Therapy

Xu F (1998) discloses the application of specific thread-burying method to points such as Dachangshu, Tianshu and Zusanli, specifically with the chorda chirurgicalis in a 2-~3 size monthly, the result of which is merit in comparison with Western medicine.

Li LSh (1998) discloses the application of Qi-gong and acupuncture to the treatment of UC. And the effective rates of both the acupunctural and Qi-gong treatment reach 57%.

To sum up, though the acupunctural therapy achieves a certain therapeutic effect, there still exists defect as follows: 1) lacks stringent scientific design; 2) with respect to the long-term therapeutic effect of said disease, the acupunctural treatment is not satisfying.

Traditional Chinese Therapy

Traditional Chinese therapy deems that the cause of mentioned disease mainly relates to the Six evils attacking, especially the evil of Damp-heat, impairment by overeating, the stagnation of emotions and congenital deficiency and the like. The mechanism is Fundamental deficiency and Incidental excess, with deficiency and excess admixed. Taking advantage of the method of planning treatment according to diagnosis, the traditional Chinese medicine made some progress in the treatment of UC, comprising the follows:

1) Oral Administration of Traditional Chinese Medical Materials

Shao ShQ (2000) discloses that the oral administration of XiLei powder and coix seed in the treatment of UC by using the method of nourishing stomach and invigorating spleen achieves a satisfying therapeutic result.

Tian ZhX (2000) discloses the administration of Prepared Aconite Root and Chinese Cassia Tree-bark etc., for the treatment of spleen yang-deficient UC with a total effective rate of 95.5%.

Zhou JH (2000) discloses the oral administration of Coptis Root and Common Fennel etc., in the treatment of chronic UC with a total effective rate of 88%.

It can be seen that the oral administration methods disclosed as above has achieved good treatment effect. However, since the UC pathogenic site mainly locates on the terminal end of intestine, if merely treat by means of oral administration with the method of planning treatment according to diagnosis, it is hard for the pharmaceutical effect to focus on the pathogenic place. Therefore, soly treating by means of oral administration is insufficiently beneficiary to the direct treatment to pathogenic site.

2) Enteroclytic Treatment of Traditional Chinese Medicinal Materials

Zhong GSH (1996) discloses that the enteroclysis of Dandelion herb and Can Er etc., in the treatment of UC achieves a satisfying therapeutic result is satisfying.

Wang BH (1992) discloses that a satisfying result was obtained by applying the enteroclysis of Meihua Dianshe Dan plus other traditional Chinese medicinal materials for the treatment of UC.

Leng W (1996) discloses that the total efficacy of the enteroclysis of Yunnan White powder combined with XiLei powder for the treatment of UC reaches 97%.

Chinese patent application No. 97125835.X (for the powder for the treatment of UC and proctitis) employs the raw materials like Pearl, Coptis Root, Sanguis Draxonis (Xue Jie) and Rhubarb etc., for the treatment of said disease with certain therapeutic effects achieved.

At present, the pathogenesis of UC is still unknown. Some experiences for treating this disease by TCM have been accumulated. Although the aforesaid therapies for treating this disease has achieved certain effects, they mainly focus on clearing away toxic material, promoting regeneration of tissue, promoting blood circulation and removing blood stasis, without giving a symptomatic treatment to the UC induced by the stagnation of Damp-heat. In addition, the absence of staging and follow-up study of long-term effect as well as the prevention of relapse of said disease, without unified therapeutic scheme brings difficulties to further R&D of effective medicament.

DESCRIPTION OF THE INVENTION

The present invention overcomes the defects of present art. It provides a formulation of traditional Chinese medicinal materials for the treatment of UC with excellent short-, long-term therapeutic effects, comprising eight sorts of traditional Chinese medicinal materials, and the preparation method thereof. On the basis of removing heat, promoting blood circulation, eliminating dampness and promoting tissue regeneration, the preparation of traditional Chinese medicinal materials according to this invention is administrated by enteroclysis, in a form of suspension, and delivers the medicaments to the nidus. Said preparation brings the effects of exterior detoxification, elimination of dampness and regeneration of tissue by increasing the blood concentration of medicament in the lesions, protecting the ulcerative surface of intestine, promoting the localized blood circulation, and accelerating the resolution of inflammation and the healing of ulcer. The invention further achieves the whole-body effect of clearing away heat and toxic material, promoting blood circulation and removing blood stasis by maintaining a certain level of drug blood concentration through passive diffusion.

The purpose of the invention can be achieved with the following embodiments.

The preparation of traditional Chinese medicinal materials for the treatment of UC comprises the raw materials as 1-10 wt % of Sanguis Draxonis, 15-40 wt % of Radix Paeoniae Rubra (Chi Shao), 1-20 wt % of Indigo Naturalis (Qing Dai), 1-10 wt % of Halloysitum Rubrum (Chi Shi Zhi), 15-40 wt % of Catechu (Er Cha), 1-10 wt % of Calcined Alumen (Ku Fan), 5-30 wt % of Rhizoma Bletillae (Bai Ji) and 1-10 wt % of Calamina (Lu Gan Shi).

The preparation of traditional Chinese medicinal materials preferably comprises the raw materials as 3-7 wt % of Sanguis Draxonis, 25-35 wt % of Radix Paeoniae Rubra, 5-15 wt % of Indigo Naturalis, 1-5 wt % of Halloysitum Rubrum, 25-35 wt % of Catechu, 1-5 wt % of Calcined Alumen, 10-20 wt % of Rhizoma Bletillae and 1-5 wt % of Calamina.

The preparation of traditional Chinese medicinal materials mostly preferably comprises the raw materials as 5.1 wt % of Sanguis Draxonis, 30 wt % of Radix Paeoniae Rubra, 10 wt % of Indigo Naturalis, 3 wt % of Halloysitum Rubrum, 30 wt % of Catechu, 3 wt % of Calcined Alumen, 15 wt % of Rhizoma Bletillae and 3 wt % of Calamina.

The processed method of the preparation of traditional Chinese medicinal materials for the treatment of UC comprises the steps as follows:

(a) Providing the raw materials as follows: 1-10 wt % of Sanguis Draxonis, 15-40 wt % of Radix Paeoniae Rubra, 1-20 wt % of Indigo Naturalis, 1-10 wt % of Halloysitum Rubrum, 15-40 wt % of Catechu, 1-10 wt % of Calcined Alumen, 5-30 wt % of Rhizoma Bletillae and 1-10 wt % of Calamina;

(b) Macerating and decocting three of the provided materials: Radix Paeoniae Rubra, Catechu and Calcined Alumen with water for 2-4 times, and the aqueous decoction is combined, filtered, stored in low temperature, concentrated and stored for available;

(c) Mixing the provided materials Indigo Naturalis and Sanguis Draxonis homogeneously, stirring with PEG solution added for available;

(d) Pulverizing the provided material Rhizoma Bletillae with potassium sorbate finely, admixing it with the above-mentioned aqueous decoction, the Indigo Naturalis and Sanguis Draxonis in PEG (polyethylene glycol) solution, and the provided materials Halloysitum Rubrum and Calamina, then grinding the resultant mixture homogenously and making it up with water to produce the preparation.

In step (b), the time for maceration is 0.5-1 hour; the ratio of water and raw materials being added is 10-14:1; the time being stored at a low temperature is 44-52 hours; 1 liter of the filtrated aqueous decoction is concentrated from 0.30-0.36 kilogram of the raw materials. In addition, the said PEG solution according to step (c) is the solution of PEG 400 mixed with tragacanth, and the particle size of Rhizoma Bletillae and potassium sorbate after being pulverized is 150 μm in step (d).

The PEG is PEG 400, dispensing in 70~90 ml per bottle.

By applying the modern specific extracting technology and the high-tech quality control means, the invention improves the content and quality control standard of the active ingredients, to provide a real guarantee for the safety and therapeutic efficiency of said preparation. The preferable dosage form of this invention is enema. Since the lesion of UC locates on the mucosa of colon, the enema can be administrated directly to said location, retained for a long time and in a high concentration, for the benefit of the absorbance of medicament and the therapeutic effect being carried out. In particular, the traditional Chinese medicinal materials selected in this invention, characterized with the effect of astringing and promoting tissue regeneration, are very suitable for the treatment of UC, therefore a satisfying effect is achieved as approved by the clinical practice.

The invention is characterized by applying some traditional Chinese medicinal materials for exterior use, by treating UC with the traditional Chinese medicinal materials effective in "exterior sore", the effects of removing the putrid tissues and promoting the tissue regeneration are achieved, i.e. "treating exterior sore from within". Complying with the principles that "external therapy equals to internal therapy in traditional Chinese Medicine, the traditional Chinese medicinal materials for external use are also for internal use", some traditional Chinese medicinal materials for external uses or having good external effects have been selected, including Sanguis Draxonis, Indigo Naturalis, Catechu and Calamina and the like, in which the Calamina possesses the effects of extoxicating, ulcer-healing, dampness-astringing, antisepsis and promoting the regeneration of tissue; and in which the Catechu have the effects of dampness-astringing and ulcer-healing in the treatment of Dysentery. In this invention, the optical treatment effects of high-effectiveness and efficiency are achieved by means of external enterolysis, with the traditional Chinese medicinal materials being directed to the nitus and a high concentration being retained.

By illustrating the following studies in the tests carried on animals and with regards to toxicity of the preparation of traditional Chinese medicinal materials in the present invention, the beneficiary effect of this invention are set forth hereinafter:

Study in the Pharmacodynamics of the Traditional Chinese Medicinal Materials in the Invention 1) Prevention and Curative Effect for the Rat Model Having Acute Ulterative Colitis Caused by Acetic Acid The symptoms of the acetic acid-induced UC rat model and the patient with UC in acute phase are similar, including mucous or bloody stool, dropsy of colon, thinning of colon paries, hemorrhage and erosion and so on; meanwhile, extensive necrosis of colon mucosa and obvious infiltration of neutrophilic leucocytes to individual layer of colon mucosa were microscopically observed. A continuous administration of the preparation of traditional Chinese medicinal materials in the present invention in a dosage of 0.25-1 g raw material/kg for 10 days would markedly alleviate the above-mentioned colonic pathological changes, and have a good protecting and repairing effect for the lesion in colon mucosa.

2) Prevention and Curative Effect for the Rat Model Having UC Induced by 2,4-DNCB After the attack of 2,4-DNCB, colon mucosa demonstrates an inflammatory reaction mainly with ulcer. The lesion of colon shown in the model is restricted in the range, but severe in degree; therefore, it suits for the evaluation of the therapeutic effect of the test preparation. In a dosage of 0.5-2 g raw material/kg, the administration of the preparation of traditional Chinese medicinal materials for prevention or treatment, significantly decreases the incidence rate of ulcer in a large area of colon mucosa, from the damage to mucosa mainly in superficial or localized types, a rather good anti-ulcer effect is proved. As a result, it revealed that this preparation has an undoubted effect on UC caused by allergic inflammation.

3) Prevention and Cure Effect for the Rat Model Having UC with the Replication of *E. coli*

The model rat having UC with the replication of *E. coli* is similar to the UC patients in symptoms, course of disease and tissue changes. Said model is much closer to the natural conditions since its antigen is among the normal flora of the intestine. From the model rat, it is observed that the circulating immunocomplex is increased, and the occurrence and existence of which turns into the pathological basis of UC. During the treating course, the preparation of traditional Chinese medicinal materials according to this invention, in a dosage of 0.5-2 g raw material/kg, will reverse the abnormal aforesaid serum detection index in the rat model and improve the corresponding historical changes of colon obviously, thereby repair the lesion in mucosa.

4) The Anti-Inflammatory Effect

The preparation of traditional Chinese medicinal materials of this invention possesses a good effect of anti-inflammation on both acute inflammatory edema and chronic proliferating inflammation, which is indispensable to the treatment of intestinal inflammation caused by UC.

5) The Analgesic and Antispasmodic Effect

The preparation of traditional Chinese medicinal materials of this invention is observed to possess an obvious analgesic effect, which lasts for a long time, in the tests of acetic acid induced twitching test and water bath tail flicking test in mice. In addition, said preparation has an obvious antispasmodic effect on the ileum of Guinea pig.

6) The Bacteriostatic and Sterilizing Effect

The preparation of traditional Chinese medicinal materials according to this invention has a good bacteriostatic and sterilizing effect on five kinds of bacteria, which is often seen in the intestine.

Study in the Toxicity of the Traditional Chinese Medicinal Materials in the Invention 1) Acute Toxicity Test The test preparation, enema of the preparation of traditional Chinese medicinal materials according to this invention is administrated to the colon of mice in one day (twice per day), in a dosage of 18.6 g raw material/kg. From a 7-day consecutive observation after the administration, none toxicity test is observed, and a total of 20 mice are alive and grow normally. The maximum tolerated dose for the colon administration of said preparation is 18.6 g raw material/kg.

2) Stimulus Test to the Intestine Mucosa of Rat

The enema of the preparation of traditional Chinese medicinal materials according to this invention is administrated to the colon of rat in 3.8 g raw material/kg. The 24-hour, 48-hour and 7-day observation of the reaction of intestine mucosa in the rat show that said edema does not stimulate the mucosa obviously, hereby can be administrated to the clinics safely.

3) Long-Term Toxicity Test

The enema of the preparation of traditional Chinese medicinal materials according to this invention is administrated to the colon of rat in 2.2 g raw material/kg and 1.1 g raw material/kg daily, for a successive three months. From the observation of the general drug reaction, detection hematological, hematological biochemical and patho-histological indexes, no obvious toxicity reaction involving drugs are observed, each index being essentially the same as the control group. These data demonstrates that said preparation is less toxic in the administration to the colon, thereby is quite safe in the clinical administration.

EXAMPLES

The following examples will be further provided for the illustration, which is not for the limitation of present invention.

Example 1

(a) The preparation is provided comprising 14 g of Sanguis Draxonis, 84 g of Radix Paeoniae Rubra, 28 g of Indigo Naturalis, 8.4 g of Halloysitum Rubrum, 84 g of Catechu, 8.4 g of Calcined Alumen, 42 g of Rhizoma Bletillae and 8.4 g of Calamina;

(b) Radix Paeoniae Rubra, Catechu and Calcined Alumen are decocted by macerating Radix Paeoniae Rubra, Catechu and Calcined Alumen for 0.5 hour and decocting with water for 2 each for 1 hour, the aqueous decoction is then combined, filtered, stored at low temperature, refiltered and concentrated to 600-1000 ml;

(c) The Indigo Naturalis, Sanguis Draxonis in PEG solution is prepared as follows: mixing 1.5 g of the Indigo Naturalis, Sanguis Draxonis and tragacanth in 28 ml of PEG-400 thoroughly by stirring, and adding said solution to the preceding concentrated decoction for available;

(d) The addition of the pulverized Rhizoma Bletillae is as follows: grinding 2 g of the pulverized(in a particle size of 150 μm) Rhizoma Bletillae and potassium sorbate homogenously, then adding it to the available solution obtained from step(c);

(e) The addition of Halloysitum Rubrum and Calamina is as follows: grinding Halloysitum Rubrum and Calamina together and adding it to the solution from step (d), making up with water to 1000 ml, and grinding thoroughly, dispensing and sterilizing the solution obtained to produce the preparation.

It should be noted that the preparation is viscid suspension in Reddish-brown; the precipitate will be seen after a long standing; and the preparation will disperse immediately after being shaken.

Example 2

The preparation is provided comprising 22.1 g of Sanguis Draxonis, 69 g of Radix Paeoniae Rubra, 25 g of Indigo Naturalis, 25 g of Halloysitum Rubrum, 69 g of Catechu, 17 g of Calcined Alumen, 28 g of Rhizoma Bletillae and 22.1 g of Calamina;

The processed steps (b)-(e) hereof refer to Example 1.

Example 3

The preparation is provided comprising 19 g of Sanguis Draxonis, 67 g of Radix Paeoniae Rubra, 27.1 g of Indigo Naturalis, 19 g of Halloysitum Rubrum, 67 g of Catechu, 14.1 g of Calcined Alumen, 47 g of Rhizoma Bletillae and 17 g of Calamina;

The processed steps (b)-(e) hereof refer to Example 1.

Example 4

The preparation is provided comprising 11 g of Sanguis Draxonis, 91 g of Radix Paeoniae Rubra, 19 g of Indigo Naturalis, 14 g of Halloysitum Rubrum, 91 g of Catechu, 12.2 g of Calcined Alumen, 28 g of Rhizoma Bletillae and 11 g of Calamina;

The processed steps (b)-(e) hereof refer to Example 1.

Example 5

The preparation is provided comprising 8 g of Sanguis Draxonis, 97 g of Radix Paeoniae Rubra, 14 g of Indigo Naturalis, 6 g of Halloysitum Rubrum, 97 g of Catechu, 2.2 g of Calcined Alumen, 47 g of Rhizoma Bletillae and 6 g of Calamina;

The processed steps (b)-(e) hereof refer to Example 1.

What is claimed is:

1. A preparation of traditional Chinese medicinal materials for the treatment of ulcerative colitis, characterized in comprising the raw materials as 1-10 wt % of Sanguis Draxonis, 15-40 wt % of Radix Paeoniae Rubra, 1-20 wt % of Indigo Naturalis, 1-10 wt % of Halloysitum Rubrum, 15-40 wt % of Catechu, 1-10 wt % of Calcined Alumen, 5-30 wt % of Rhizoma Bletillae and 1-10 wt % of Calamina.

2. The preparation of traditional Chinese medicinal materials for the treatment of ulcerative colitis according to claim 1, characterized in comprising the raw materials as 3-7 wt % of Sanguis Draxonis, 25-35 wt % of Radix Paeoniae Rubra, 5-15 wt % of Indigo Naturalis, 1-15 wt % of Halloysitum Rubrum, 25-35 wt % of Catechu, 1-5 wt % of Calcined Alumen, 10-20 wt % of Rhizoma Bletillae and 1-5 wt % of Calamina.

3. The preparation of traditional Chinese medicinal materials for the treatment of ulcerative colitis according to claim 1, characterized in comprising the raw materials as 5.1 wt % of Sanguis Draxonis, 30 wt % of Radix Paeoniae Rubra, 10 wt % of Indigo Naturalis, 3 wt % of Halloysitum Rubrum, 30 wt % of Catechu, 3 wt % of Calcined Alumen, 15 wt % of Rhizoma Bletillae and 3 wt % of Calamina.

4. A method for preparing a preparation of traditional Chinese medicinal materials for the treatment of ulcerative colitis, characterized in comprising the steps of:
a) Providing the raw materials as follows: 1-10 wt % of Sanguis Draxonis, 15-40 wt % of Radix Paeoniae Rubra, 1-20 wt % of Indigo Naturalis, 1-10 wt % of Halloysitum Rubrum, 15-40 wt % of Catechu, 1-10 wt % of Calcined Alumen, 5-30 wt % of Rhizoma Bletillae and 1-10 wt % of Calamina;
b) Macerating three of the provided materials: Radix Paeoniae Rubra, Catechu and Calcined Alumen into water and decocting 2-4 times, the aqueous decoction is combined, filtered, stored in a fridge, concentrated and stored for later use;
c) Mixing the provided materials Indigo Naturalis and Sanguis Draxonis homogeneously, stirring with PEG solution added for later use; and
d) Pulverizing the provided material Rhizoma Bletillae with potassium sorbate finely, admixing it with the above-mentioned aqueous decoction, the Indigo Naturalis and Sanguis Draxonis in PEG solution, and the provided materials Halloysitum Rubrum and Calamina, then grinding the resulting mixture homogenously and making it up with water to produce the preparation.

5. The method according to claim 4, wherein the time for maceration in step b) is from 30 min to 1 hour.

6. The method according to claim 4, wherein step b), the ratio of water: raw materials is from 10:1 to 14:1.

7. The method according to claim 4, wherein the aqueous decoction in step b) is stored in the refrigerator for 44 to 52 hours.

8. The method according to claim 4, wherein 1 liter of the filtrated aqueous decoction is concentrated from 0.30-0.36 kg of the raw materials in step b).

9. The method according to claim 4, wherein the PEG solution in step c) is the solution of PEG 400 dissolved with tragacanth.

10. The method according to claim 4, wherein the particle size of Rhizoma Bletillae and potassium sorbate in step d) is 150 μm.

11. The method according to claim 4, wherein the preparation is in the form of enema.

12. A method of making a medicament comprising providing the preparation of claim 1 in a pharmaceutically acceptable form.

13. The preparation according to claim 1, characterized in being in the form of enema.

14. The preparation according to claim 2, characterized in being in the form of enema.

15. The preparation according to claim 3, characterized in being in the form of enema.

* * * * *

UNITED STATES PATENT AND TRADEMARK OFFICE
CERTIFICATE OF CORRECTION

| | | |
|---|---|---|
| PATENT NO. | : 7,354,570 B2 | Page 1 of 1 |
| APPLICATION NO. | : 10/507149 | |
| DATED | : April 8, 2008 | |
| INVENTOR(S) | : Bihui Wang et al. | |

It is certified that error appears in the above-identified patent and that said Letters Patent is hereby corrected as shown below:

Cover page, item (54) "CHINESE PREPARATION FOR TREATING ENTERITIS ULCER COLITIS AND PREPARATION METHOD THEREOF" should be replaced with -- A PREPARATION OF TRADITIONAL CHINESE MEDICINAL MATERIALS FOR TREATING ULCERATIVE COLITIS AND THE PROCESSED METHOD THEREOF --.

Column 1, line 1, "CHINESE PREPARATION FOR TREATING ENTERITIS ULCER COLITIS AND PREPARATION METHOD THEREOF" should be replaced with -- A PREPARATION OF TRADITIONAL CHINESE MEDICINAL MATERIALS FOR TREATING ULCERATIVE COLITIS AND THE PROCESSED METHOD THEREOF --.

Signed and Sealed this

Second Day of September, 2008

JON W. DUDAS
*Director of the United States Patent and Trademark Office*